US007019182B2

(12) United States Patent
Grosso

(10) Patent No.: US 7,019,182 B2
(45) Date of Patent: Mar. 28, 2006

(54) METHOD OF HYDROCARBON PRESERVATION AND ENVIRONMENTAL PROTECTION

(75) Inventor: Philip Grosso, Auburn, CA (US)

(73) Assignee: GRT, Inc., The Woodlands, TX (US)

( * ) Notice: Subject to any disclaimer, the term of this patent is extended or adjusted under 35 U.S.C. 154(b) by 0 days.

(21) Appl. No.: 10/958,519

(22) Filed: Oct. 4, 2004

(65) Prior Publication Data

US 2005/0043572 A1 Feb. 24, 2005

Related U.S. Application Data

(63) Continuation-in-part of application No. 10/894,165, filed on Jul. 19, 2004, which is a continuation-in-part of application No. 10/369,148, filed on Feb. 19, 2003, which is a continuation of application No. 10/114,579, filed on Apr. 2, 2002, now Pat. No. 6,525,230, which is a continuation-in-part of application No. 09/951,570, filed on Sep. 11, 2001, now Pat. No. 6,462,243.

(60) Provisional application No. 60/284,642, filed on Apr. 18, 2001.

(51) Int. Cl.
C07B 41/02 (2006.01)

(52) U.S. Cl. .................. 568/910.5; 568/910; 585/240; 585/302

(58) Field of Classification Search ............ 568/910.5, 568/910; 585/240, 302
See application file for complete search history.

(56) References Cited

U.S. PATENT DOCUMENTS

| 3,172,915 A | 3/1965 | Borkowski et al. | |
| 3,273,964 A | 9/1966 | Rosset | |
| 3,310,380 A | 3/1967 | Lester | |
| 3,353,919 A | 11/1967 | Lester | 23/216 |
| 3,894,107 A | 7/1975 | Butter et al. | 260/668 |
| 4,006,169 A | 2/1977 | Anderson et al. | 260/348 |
| 4,301,253 A | 11/1981 | Warren | 518/700 |
| 4,333,852 A | 6/1982 | Warren | 252/429 |
| 4,373,109 A | 2/1983 | Olah | 585/640 |
| 4,440,871 A | 4/1984 | Lok et al. | 502/214 |
| 4,465,893 A | 8/1984 | Olah | 585/709 |
| 4,496,752 A | 1/1985 | Gelbein et al. | 549/521 |
| 4,513,092 A | 4/1985 | Chu et al. | 502/71 |
| 4,523,040 A | 6/1985 | Olah | 568/671 |
| 4,654,449 A | 3/1987 | Chang et al. | 570/261 |
| 4,769,504 A | 9/1988 | Noceti et al. | 585/415 |
| 4,795,843 A | 1/1989 | Imai et al. | 585/408 |
| 4,982,024 A | 1/1991 | Lin et al. | 570/262 |
| 5,087,786 A | 2/1992 | Nubel et al. | 585/500 |
| 5,243,098 A | 9/1993 | Miller et al. | 568/893 |
| 5,276,240 A | 1/1994 | Timmons et al. | |
| 5,334,777 A | 8/1994 | Miller et al. | 568/859 |
| 5,486,627 A | 1/1996 | Quarderer, Jr. et al. | 549/521 |
| 5,998,679 A | 12/1999 | Miller | 568/859 |
| 6,403,840 B1 | 6/2002 | Zhou et al. | 568/579 |
| 6,452,058 B1 | 9/2002 | Schweizer et al. | 570/223 |
| 6,465,696 B1 | 10/2002 | Zhou et al. | 568/671 |
| 6,465,699 B1 | 10/2002 | Grosso | 568/893 |
| 6,472,572 B1 | 10/2002 | Zhou et al. | 568/893 |
| 6,486,368 B1 | 11/2002 | Sherman et al. | |
| 6,525,230 B1 | 2/2003 | Grosso | 568/891 |
| 6,713,087 B1 | 3/2004 | Tracy et al. | 424/486 |
| 2002/0198416 A1 | 12/2002 | Zhou et al. | 568/910 |
| 2003/0069452 A1 | 4/2003 | Sherman et al. | 568/694 |
| 2003/0078456 A1 | 4/2003 | Yilmaz et al. | 568/488 |
| 2003/0120121 A1 | 6/2003 | Sherman et al. | 568/800 |
| 2003/0125585 A1 | 7/2003 | Yilmaz et al. | 568/490 |
| 2003/0166973 A1 | 9/2003 | Zhou et al. | 568/488 |
| 2004/0006246 A1 | 1/2004 | Sherman et al. | 568/470 |

FOREIGN PATENT DOCUMENTS

| BR | 0210054 | 8/2004 |
| CA | 2447761 | 11/2002 |
| CA | 2471295 | 7/2003 |
| EP | 1395536 | 3/2004 |
| EP | 1404636 | 4/2004 |
| EP | 1435349 | 7/2004 |
| EP | 1474371 | 11/2004 |
| JP | 2004-529189 | 9/2004 |
| WO | WO 00/07718 | 2/2000 |
| WO | WO 00/09261 | 2/2000 |
| WO | WO 02/094751 | 11/2002 |
| WO | WO 03/000635 | 1/2003 |
| WO | WO 03/022827 | 3/2003 |
| WO | WO 03/062172 | 7/2003 |

OTHER PUBLICATIONS

CI Coupling via bromine activation and tandem catalytic condensation and neutralization over CaO/zeolite composites; Ivan Lorkovic, et al.; The Royal Society of Chemistsry 2004; Chem. Commun. 2004, pp. 566-567.

Ionic Bromination of Ethane and Other Alkanes (Cycloalkanes) with Bromine Catalyzed by the Polyhalomethane 2A1Br3 Aprotic Organic Superacids under Mild Conditions; Irena S. Akhren, et al.; Tetrahedron Letters, vol. 36, No. 51, pp. 9365-9368,1995.

Selective bromination of alkanes and arylalkanes with CBr4; Vladimir V. Smirnov, et al., Mendeleev Communications Electronic Version, Issue 5, 2000 (pp. 167-206).

(Continued)

Primary Examiner—Elvis O. Price
(74) Attorney, Agent, or Firm—Christie, Parker & Hale, LLP

(57) ABSTRACT

Gas phase hydrocarbons resulting from the operation of offshore petroleum wells are converted into corresponding liquid products which are mixed with liquid phased hydrocarbons resulting from operation of the offshore petroleum well for delivery therewith.

1 Claim, 2 Drawing Sheets

OTHER PUBLICATIONS

Selective Monohalogenation of Methane over Supported Acid or Platinum Metal Catalysts and Hydrolysis of Methyl Halides over y-Alumina-Supported Metal Oxide/Hydroxide Catalysts. A Feasible Path for the Oxidative Conversion of Methane into Methyl Alcohol/Dimethyl Ether; George B. Olah, et al.; Contribution from the Donald P. and Katherine B. Loker Hydrocarbon Research Institute and Department of Chemistry, University of Southern California, Los Angeles, CA; received Apr. 22, 1985 (J. Am. Chem. Soc. 1985, 107, 7097-7105).

Electrophilic Methane Conversion; by George A. Olah; Acc. Chem. Res. 1987, 20, 422-428, Loker Hydrocarbon Research Institute and Department of Chemistry, University of Southern California, Los Angeles, California.

Antimony Pentafluoride/Graphite Catalyzed Oxidative Carbonylation of Methyl Halides with Carbon Monoxide and Copper Oxides (or Copper/Oxygen) to Methyl Acetate; by George A. Olah and Jozef Bukala; J. Org. Chem., 1990, 55, No. 14, 4293-4297; Donald P. and Katherine B. Loker Hydrocarbon Research Institute and Department of Chemistry, University of Southern California, University Park, Los Angeles, California.

Superacid-Catalyzed Carbonylation of Methane, Methyl Halides, Methyl Alcohol, and Dimethyl Ether to Methyl Acetate a Acetic Acid; by Alessandro Bagno, Jozef Bukala, and George A. Olah; J. Org. Chem. 1990, vol. 55, No. 14, 4284-4292; Donald P. and Katherine B. Loker Hydrocarbon Research Institute, University of Southern California, University Park, Los Angeles, California.

Ylide chemistry. 1. Bifunctional acid-base-catalyzed conversion of heterosubstituted methanes into ethylene and derived hydrocarbons. The onium-ylide mechanism of the C1→C2 conversion by George A. Olah et al. (J. Am. Chem. Soc. 106, 2143-2149 (1984)).

Grignard Reagents with Transition Metal Halides: Disproportionation, and Exhange with Olefins; by Masuhiko Tamura and Jay K. Kochi, Bulletin of the Chemical Society of Japan, v. 44, 1971 pp. 3063-3073.

The Catalytic Dehydrohalogenation of Haloethanes on Solid Acids and Bases, Mochida, et al., Bulletin of the Chemical Society of Japan, vol. 44, 3305-3310, 1971.

Nanocrystalline Ultra High Surface Area Magnesium Oxide as a Selective Base Catalyst, Ryan Richards, et al., Scripta Materialia, 44, 2001, pp. 1663-1666.

Nanocrystal Metal Oxide-Chlorine Adducts: Selective Catalysts for Chlorination of Alkanes, Naijian Sun and Kenneth J. Klabunde, J. Am. Chem. Soc., 1999, 121, 5587-5588.

Nanocrystalline MgO as a Dehydrohalogenation Catalyst, Iiya V. Mishakov, et al., Journal of Catalysis 206, 40-48, 2002.

Reactions of VX, GD, and HD with Nanosize CaO: Autocatalytic Dehydrohalogenation of HD, George W. Wagner, et al., J. Phys. Chem. B. 2000, 104, 5118-5123.

Changes in Texture and Catalytic Activity of Nanocrystalline MgO during Its Transformation to $MgCl_2$ in the Reaction with 1-Chlorobutane, Kenneth J. Klabunde, et al., J. Phys. Chem. B. 2001, 105, 3937-3941.

http://webbook.nist.gov/.

Monomethyl-Branching of Long n-Alkanes in the Range from Decane to Tetracosane on Pt/H-ZSM-22 Bifunctional Catlayst, Marion C. Claude and Johan A. Martens, Journal of Catalysts 190, pp. 39-48 (2000).

Synthesis and Characterization of a Catalytically Active Nickel-Silicoaluminophosphate Catalyst for the Conversion of Methanol to Ethene; J.M. Thomas, Y Xu, C.R.A.. Catlow, and J.W. Couves; Chem. Mater. 1991, 3, 667-672.

Catalytically active centres in porous oxides: design and performance of highly selective new catalysts; John Meurig Thomas and Robert Raja; The Royal Society of Chemistry 2001, Chem. Commun., 2001, 675-687.

METHOD OF HYDROCARBON PRESERVATION AND ENVIRONMENTAL PROTECTION

CROSS-REFERENCE TO RELATED APPLICATIONS

This is a continuation-in-part application under 37 C.F.R. §1.63 of application Ser. No. 10/894,165 filed Jul. 19, 2004, currently pending, which is a continuation-in-part of application Ser. No. 10/369,148 filed Feb. 19, 2003, currently pending; which is a continuation application of application Ser. No. 10/114,579, filed Apr. 2, 2002, now. U.S. Pat. No. 6,525,230; which is a continuation-in-part application of application Ser. No. 09/951,570 filed Sep. 11, 2001, now U.S. Pat. No. 6,462,243, claiming priority based on provisional Application Ser. No. 60/284,642 filed Apr. 18, 2001.

TECHNICAL FIELD

This invention relates generally to preventing waste of valuable hydrocarbons and to preventing air pollution, and more particularly to utilization of gaseous hydrocarbons resulting from the operation of offshore petroleum wells that would otherwise be flared.

BACKGROUND AND SUMMARY OF THE INVENTION

The recovery of petroleum products at offshore locations is well known. Offshore oil platforms are highly efficient in the handling and delivery of liquid hydrocarbons recovered from beneath the sea. However, because of the expense involved in managing, storing, and transporting gas phase hydrocarbons often exceeds the value thereof, gaseous hydrocarbons resulting from the operation of offshore petroleum wells are often flared.

The burning of gaseous hydrocarbons at offshore locations is disadvantageous for at least two reasons. First, valuable hydrocarbons are wasted. Second, depending on the direction of prevailing winds and the location of particular offshore petroleum wells relative to populated areas, the burning of gaseous hydrocarbons may result in environmental concerns.

The present invention comprises a method of hydrocarbon preservation and environmental protection which overcomes the foregoing and other problems which have long since characterized the prior art. In accordance with broader aspects of the invention, gas phase hydrocarbons resulting from the operation of offshore petroleum wells are converted into corresponding hydrocarbon compounds that are liquid, readily converted to liquid, or soluble in the liquid phase hydrocarbons produced by operation of the well, all of which are hereinafter referred to as liquid products. The resulting liquid products are mixed with liquid phase hydrocarbons resulting from operation of the offshore petroleum well for delivery therewith. In this manner wastage of gaseous hydrocarbons resulting from operation of the offshore petroleum well is eliminated as are potential environmental problems.

In accordance with more specific aspects of the invention there is provided an imperforate cylinder comprising a first zone which is initially filled with metal halide, a second zone which is initially filled with metal oxide, and a central zone located between the first and second zones which is initially empty. Oxygen or oxygen from the air is reacted with the metal halide in the first zone to produce metal oxide and halide. The halide flows from the first zone into the central zone. Simultaneously with the introduction of oxygen or air into the first zone gaseous hydrocarbons resulting from the operation of one or more offshore petroleum wells are introduced into the central zone.

Halide from the first zone reacts with the gaseous hydrocarbons to produce intermediate compounds, typically alkyl halides and hydrogen halide. The intermediate compounds pass from the central zone to the second zone. Within the second zone the intermediate compounds react with metal oxide to produce liquid products. The liquid products are then mixed with the liquid phase hydrocarbons resulting from operation of the petroleum well.

The reaction in the second zone also produces metal halide. As the foregoing process continues, substantially all of the metal halide in the first zone is converted to metal oxide, and substantially all of the metal oxide in the second zone is converted to metal halide. The direction of flow through the imperforate cylinder is then reversed and the process continues.

BRIEF DESCRIPTION OF THE DRAWINGS

A more complete understanding of the present invention may be had by reference to the following Detailed Description when taken in connection with the accompanying Drawings wherein.

DETAILED DESCRIPTION OF THE INVENTION

Figure 1:
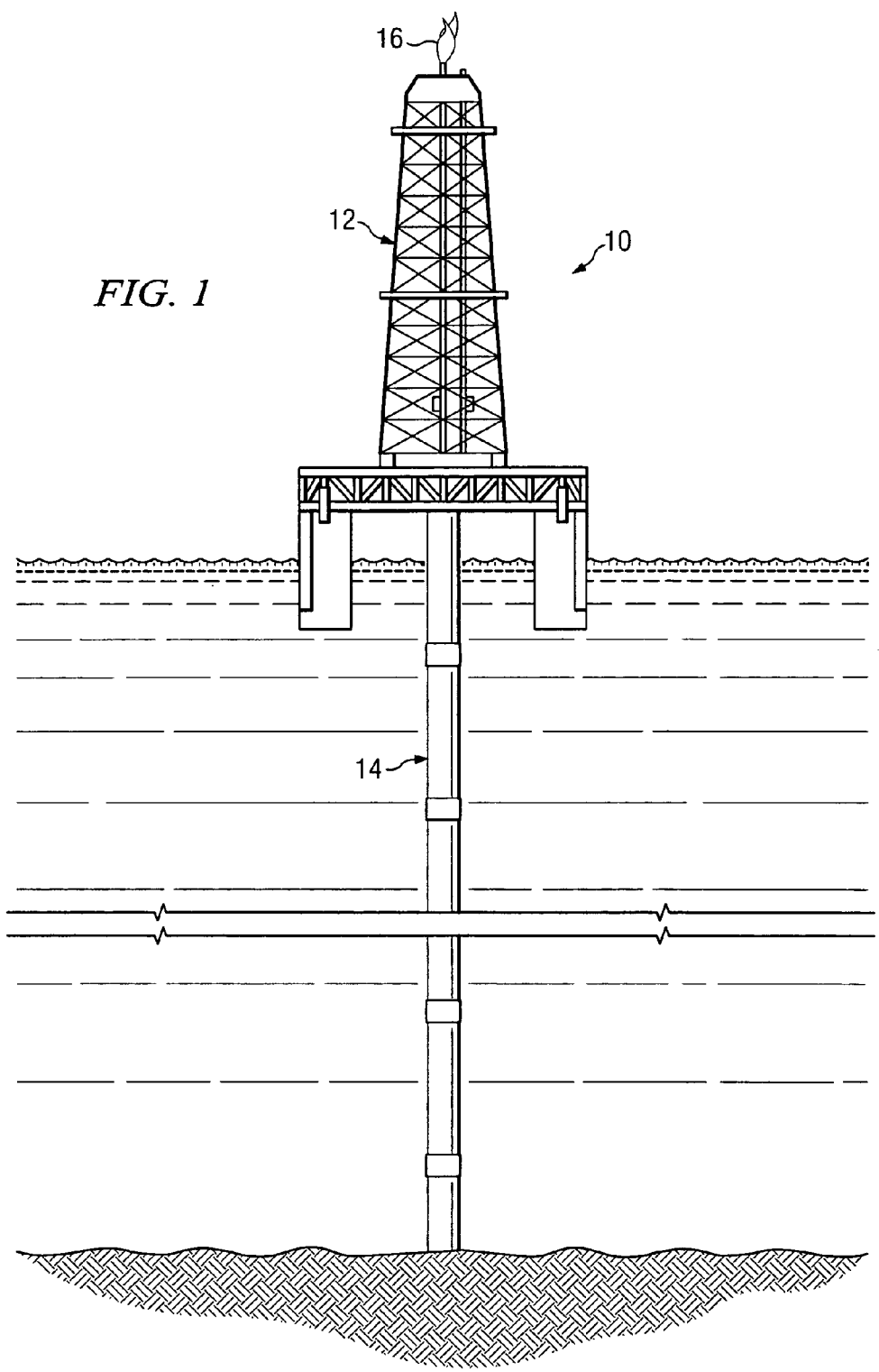
FIG. 1 is a diagrammatic illustration of an offshore petroleum production platform.

Referring to the drawings, and particularly to FIG. 1 thereof, there is shown a typical offshore petroleum production platform 10. The platform 10 is of the floating variety, it being understood that the present invention is equally applicable to other types and kinds of offshore petroleum production platforms.

The platform 10 may include a superstructure 12 extending upwardly therefrom. One or more conduits 14 extend downwardly from the platform 10 into engagement with petroleum-bearing strata situated beneath the sea floor. The function of the platform 10 is to recover petroleum from the sub-sea strata and to bring the recovered petroleum to the surface for delivery to refineries either through pipelines or via ships.

In many instances the petroleum that is recovered from sub-sea strata is comprised almost entirely of liquid phase hydrocarbons. In almost every instance, however, the petroleum that is recovered by an offshore production platform such as the production platform 10 includes some gas phase compounds. Because the expense involved in collecting, storing, and transporting the gas phase hydrocarbons from the platform 10 to a point of utilization often exceeds the value thereof, the gas phase hydrocarbons resulting from the operation of offshore wells are often flared as is indicated at 16.

The burning of gaseous hydrocarbons at offshore locations is disadvantageous for at least two reasons. First, valuable hydrocarbons are wasted. Second, depending on the direction of prevailing winds and the location of particular offshore petroleum wells relative to populated areas, the burning of gaseous hydrocarbons may result in environmental concerns.

In accordance with the present invention the practice of flaring gas phase hydrocarbons resulting from the operation of offshore petroleum wells is eliminated. In lieu thereof, the gas phase hydrocarbons are converted to corresponding liquid phase hydrocarbons, readily condensed hydrocarbon products, or hydrocarbons products that are readily soluble in the liquid phase hydrocarbons produced by the well, all of which are hereinafter referred to as liquid products. The liquid products resulting from the conversion step are mixed with the liquid phase hydrocarbons resulting directly from operation of the well and are delivered therewith to refineries or other processing facilities.

Figure 2A:
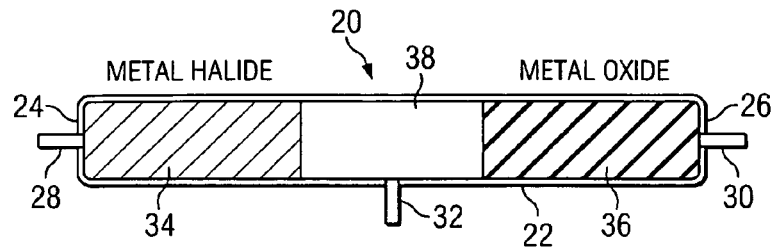
FIG. 2A is a diagrammatic illustration of an apparatus useful in the practice of the method of the present invention.

Referring to FIG. 2A an apparatus 20 useful in the practice of the method of present invention is diagrammatically illustrated. The apparatus 20 comprises an imperforate cylinder 22 which is mounted on the platform 10. The cylinder 22 is formed from an appropriate metal, an appropriate polymeric material, or both. The cylinder 22 has closed ends 24 and 26. A passageway 28 extends through the end 24 of the cylinder 22, a passageway 30 extends through the end 26 of the cylinder 22, and a passageway 32 extends to the central portion of the cylinder 22 between the ends 24 and 26 thereof.

The apparatus 20 further comprises a first zone 34 which is initially filled with metal halide, the halide comprising bromine, chlorine, iodine, or mixtures thereof. A second zone 36 located at the opposite end of the cylinder 22 from zone 34 is initially filled with metal oxide. A third or central zone 38 which is centrally disposed between the first zone 34 and the second zone 36 is initially empty.

Figure 2B:
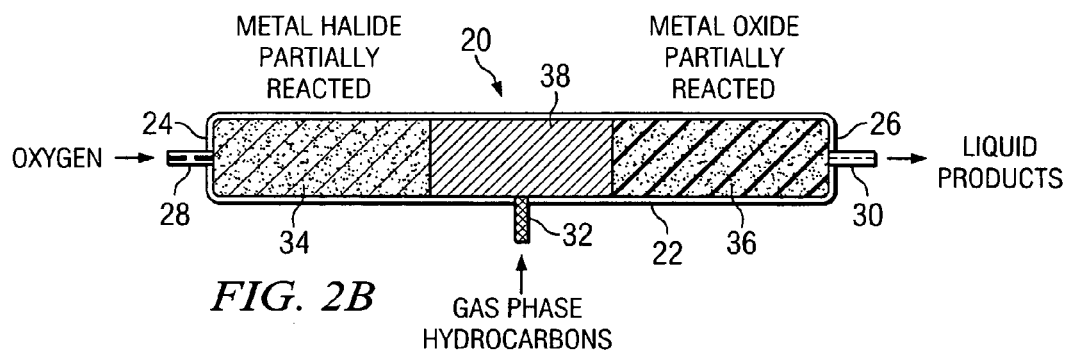
FIG. 2B is a diagrammatic illustration of a first stage in the operation of the apparatus of FIG. 2A.
Figure 2C:
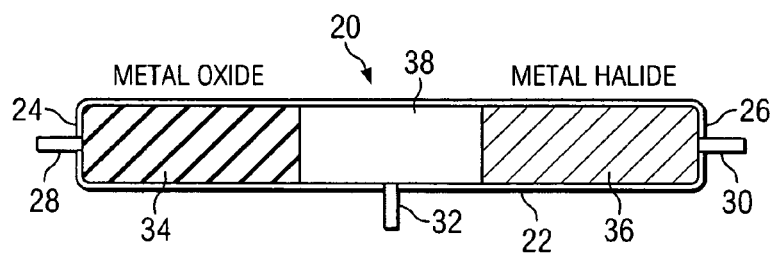
FIG. 2C is a diagrammatic illustration of a later stage in the operation of the apparatus of FIG. 2A.
Figure 2D:
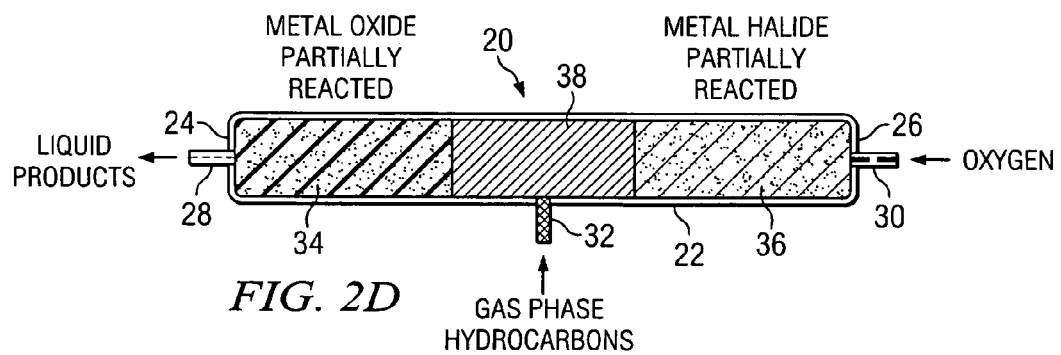
FIG. 2D is a diagrammatic illustration of a still later stage in the operation of the apparatus of FIG. 2A.

Referring to FIG. 2B, a first stage in the operation of the apparatus 20 is shown. Oxygen or air is directed into the first zone 34 through the opening 28. The oxygen or the oxygen from the air reacts with the metal halide to produce metal oxide and halide. The halide flows from the first zone 34 into the central zone 38.

Simultaneously with the introduction of oxygen or air into the first zone 34 through the opening 28, gas phase hydrocarbons, typically methane and other alkanes are directed into the central zone 38 through the opening 32. Within the central zone 38 halide reacts with gas phase hydrocarbons resulting from the operation of one or more offshore petroleum wells to produce intermediate products, typically alkyl halides and hydrogen halide. The intermediate products pass from the central zone 38 to the second zone 36.

Within the second zone 36 the intermediate products react with metal oxide to produce liquid products corresponding to the gas phase hydrocarbons that were directed into the cylinder 22 through the passageway 32. The liquid products are recovered through the passageway 30. The reaction with the second zone 36 also produces metal halide.

Referring to FIG. 4C, the foregoing reactions in the first zone 34, the central zone 38, and the second zone 36 continue until substantially all of the metal halide that was originally in the first zone 34 has been converted to metal oxide. Simultaneously, substantially all of the metal oxide that was originally in the second zone 36 is converted to metal halide. At this point the reaction is stopped and the central zone 38 is evacuated.

The next stage in the operation of the apparatus 20 is illustrated in FIG. 4D. The reactions described above in conjunction in conjunction with FIG. 4B are now reversed, with oxygen or air being admitted to the second zone 36 through the opening 30. The oxygen or oxygen from the air reacts with the metal halide in the second zone 36 to produce halide and metal oxide. The halide from the reaction in the second zone 36 passes to the central zone 38 where it reacts with gas phase hydrocarbons received through the opening 32 to produce intermediate products. The intermediate products from the reaction within the central zone passed to the first zone 34 where they react with the metal oxide contained therein to produce liquid products and metal halide. The reactions continue until substantially all of the metal halide in the second zone has been converted to metal oxide and substantially all of the metal oxide within the first zone 34 has been converted to metal halide at which time the apparatus 20 is returned to the configuration of FIG. 4A. At this point the central zone 38 is evacuated and the above described cycle of operation is repeated.

The liquid products resulting from operation of the apparatus 20 are mixed with liquid hydrocarbons resulting from operation of the offshore wells that produced the gas phase hydrocarbons. The resulting mixture is directed to refineries or other processing facilities.

Although preferred embodiments of the invention have been illustrated in the accompanying Drawing and described in the foregoing Detailed Description, it will be understood that the invention is not limited to the embodiments disclosed but is capable of numerous rearrangements, modifications, and substitutions of parts and elements without departing from the spirit of the invention.

What is claimed is:

1. A method of hydrocarbon conservation and environmental protection comprising the steps of:
   A. receiving gas phase hydrocarbons resulting from the operation of an offshore petroleum well;
   B. reacting the received gas phase hydrocarbons with a halide selected from the group consisting of bromine, chlorine, iodine, and mixtures thereof and thereby forming intermediate products;
   C. reacting the intermediate products with an oxidizer and thereby forming liquid products; and
   D. mixing the liquid products of step C. with liquid phase hydrocarbons resulting from the operation of the offshore petroleum well of step A.

* * * * *